United States Patent [19]

Sloan

[11] Patent Number: 5,001,115
[45] Date of Patent: Mar. 19, 1991

[54] PRODRUGS OF BIOLOGICALLY ACTIVE HYDROXYAROMATIC COMPOUNDS

[75] Inventor: Kenneth B. Sloan, Gainesville, Fla.

[73] Assignee: University of Florida, Gainesville, Fla.

[21] Appl. No.: 352,919

[22] Filed: May 17, 1989

[51] Int. Cl.$^5$ .................. A61K 31/70; A61K 31/595; A61K 31/535; A61K 31/255

[52] U.S. Cl. ........................... 514/34; 514/289; 514/169; 514/373; 514/222.8; 514/328; 514/360; 514/603; 514/417; 514/425; 514/518; 546/44; 546/176; 546/75; 544/2; 536/6.4; 548/123; 548/209; 548/256; 548/417

[58] Field of Search .............. 514/169, 289, 373, 417, 514/425, 222.8, 328, 360, 518, 603, 34; 536/6.4; 564/82, 155; 552/626; 546/44, 176, 75; 544/2; 548/123, 209, 256, 477, 595

[56] References Cited

PUBLICATIONS

Katritzky, et al. J. Chem. Soc. Perkin Transactions 1, 1987, pp. 781–789.
Katritzky, Tetrahedron 36, 1980 pp. 679 to 699.
Foye, Principals of Medicinal Chemistry (Philadelphia, Lea and Fibiger, 1981) p. 733.

Primary Examiner—Mukund J. Shah
Assistant Examiner—E. L. Ward
Attorney, Agent, or Firm—Kerkam, Stowell, Kondracki & Clarke

[57] ABSTRACT

Prodrugs of bio-active hydroxyaromatic drugs having the structural formula:

A pharmaceutically acceptable prodrug of a biologically active, therapeutically effective hydroxyaromatic drug, said prodrug being selected from the group consisting of, (A) compounds having the structural formula:

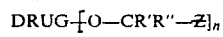

DRUG—[O—CR'R''—Z]$_n$ wherein:
DRUG —O— is the hydroxyaromatic O-dehydro residue of said drug;
R' and R' may be the same or different and may be H, alkyl, aryl or electron withdrawing groups;
Z is a displaceable leaving group; and
n is an integer in the range of from 1 to 3, and (B) pharmaceutically acceptable salts thereof.

3 Claims, No Drawings

PRODRUGS OF BIOLOGICALLY ACTIVE HYDROXYAROMATIC COMPOUNDS

BACKGROUND OF THE INVENTION

1. Field of the Invention

The present invention relates to prodrugs of therapeutic hydroxyaromatic compounds (HAC), e.g., phenols and catechols.

1. Description of the Prior Art

There are many drugs that contain phenol or catechol groups which suffer from premature metabolism at the hydroxy group during absorption after oral administration. Previous efforts to protect the hydroxy groups have been generally unsuccessful since the protecting groups employed to date are either too labile (O=COR or O=CR) or too stable (CH$_3$).

It is an object of the present invention to provide prodrugs of therapeutically effective phenols and catechols which may be administered orally and are not subject to premature metabolism but which hydrolyze readily at the intended site of treatment to release the active drug.

It is a further object of the present invention to provide a pharmaceutical composition comprising a prodrug which may be more readily orally administered than the corresponding drug.

It is a further object of the present invention to provide a therapeutic method of treatment involving the oral administration of a prodrug which has an enhanced stability over the corresponding drug.

SUMMARY OF THE INVENTION

The above and other objects are realized by the present invention which provides a pharmaceutically acceptable prodrug of a biologically active, therapeutically effective hydroxyaromatic compound (HAC), said prodrug being selected from the group consisting of, (A) compounds having the structural formula:

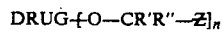

DRUG$-[$O$-$CR'R''$-$Z$]_n$ wherein: DRUG—O—is the HAC O-dehydro residue of the drug;

R' and R'' may be the same or different and are selected from the group consisting of H, cycloalkyl groups having up to 10 carbon atoms, straight or branched chain alkyl, alkenyl and alkynyl groups of 1 to 10 carbon atoms, wherein the chains thereof (1) may be interrupted by at least one N, S or O atom, or (2) may be substituted by at least one group selected from the group consisting of COR''', COOR''' and CON(R''')$_2$, hydrocarbyl aryl groups, aryl groups substituted by at least one group selected from the group consisting of COR''', COOR''', CON(R''')$_2$, N(R''')$_2$, OR''', halogen, SR''', NO$_2$ and R''', mono- and bi-cyclic saturated or unsaturated heterocyclic rings, each ring consisting of 3 to 7 members selected from the group consisting of carbon, nitrogen, oxygen and sulfur, CN, COR''', COOR''', CON(R''')$_2$ and C(halogen)$_3$;

R''' is selected from the group consisting of cycloalkyl groups having up to 10 carbon atoms, straight or branched chain alkyl, alkenyl and alkynyl groups having 1 to 10 carbon atoms, straight or branched chain alkyl, alkenyl and alkynyl groups of 1 to 10 carbon atoms wherein the chains thereof may be interrupted by at least one N, S or O atom, hydrocarbyl aryl groups, and in the case of —N(R''')$_2$ taken with the other R''' group and N is a mono- or bi-cyclic saturated or unsaturated heterocyclic ring, wherein each ring consists of 3 to 7 members selected from the group consisting of carbon, nitrogen, oxygen and sulfur;

Z is a displaceable leaving group; and n is an integer in the range of from 1 to 3, and (B) pharmaceutically acceptable salts thereof;

the prodrug having enhanced stability against premature metabolism upon oral administration and being chemically hydrolyzable to the HAC drug.

It is a further object of the invention to provide a pharmaceutical composition in unit dosage form adapted for oral administration to a human or non-human animal in need thereof comprising a therapeutically effective amount of a prodrug described above and a pharmaceutically acceptable carrier therefor.

It is still a further object of the present invention to provide a method of treatment comprising orally administering to a human or nonhuman animal in need thereof a therapeutically effective amount of a prodrug described above.

DETAILED DESCRIPTION OF THE INVENTION

The above-described prodrugs are more stable against premature metabolism than the free phenols, catechols or HAC. Although oral administration of the phenolic or catecholic drugs is greatly enhanced by the present invention, other routes of administration are also improved. The present invention permits oral dosing of drugs that must presently be administered IV thereby rendering administration of these drugs less costly and more convenient.

The above-described hydroxy-protecting groups stabilize the HAC against premature metabolism such as glucuronidation or sulfation in the gut or in the liver. As used in the present context, "premature hydrolysis" means hydrolysis before the prodrug reaches its target organ and releases the parent HAC drug. Since a prodrug (whether the mechanism of release of the parent drug is enzymatic, as in the ususal case, or chemical, as according to the present invention) releases the parent drug continually from the site of application to the target organ, 100% protection from premature hydrolysis or metabolism is unattainable. However, the chemical nature of the mechanism of release in the present invention has the advantage over enzymatic mechanisms in that it is not subject to the interpatient variability associated with the latter.

The excellent "leaving" properties of Z enable a facile chemical hydrolysis to the active drug, the rate of which depends on the chemical structure of Z and the pH of the environment. Thus, the prodrugs of the present invention are more stable at an acidic pH and would, therefore, remain relatively stable during passage through the stomach but would hydrolyze to release the parent drug more readily in the higher pH's existing, for example, in plasma. The prodrugs of the present invention are relatively stable at acidic pH's and relatively labile at basic pH's.

R' and R'' are as defined above and may be any suitable electron withdrawing group such as those described above and those referenced in J. March, "Advanced Organic Chemistry", 3d. Ed., pp. 242–250 (1985).

The term "O-dehydro residue" of a bioaffecting hydroxyaromatic compound (HAC) as used herein is intended to include those radicals that would result from removal of one or more of the protons from an OH group attached to the aromatic nucleus of an HAC, leaving a free or unsatisfied valence bond in its stead, i.e., that valence bond which defines the bridge to the Z—CR'R" moiety of the compounds of the above structural formula (A).

Representative of such radicals are:

metaraminol bitartrate residue phenylephrine hydrochloride residue diethylstilbestrol residue acetaminophen residue homosalate residue 4-hexylresorcinol residue 4-hexylresorcinol residue -continued salicylate residue diflunisal residue clamoxyquin residue morphine sulfate residue diethylstilbestrol residue 4-hexylresorcinol residue bithionol residue -continued

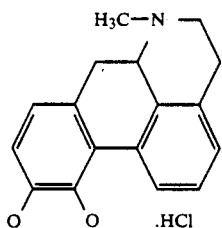

apomorphine hydrochloride residue

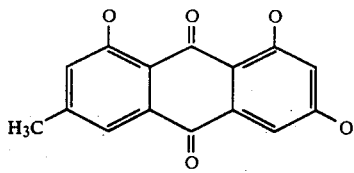

emodin residue

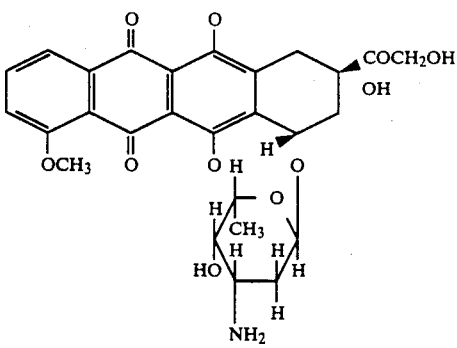

doxorubicin residue

By "pharmaceutically acceptable salt", there are intended the conventional non-toxic acid addition or quaternary ammonium salts of the compounds of the above structural formula (A), formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, fumaric, toluenesulfonic, and the like. Preferred salts of the invention are those derived from the same acids as are the generally preferred salts of the parent phenols, e.g., the hydrochlorides in the case of phenylephrine derivatives.

The pharmaceutically acceptable salts of the present invention can be synthesized from the compounds embraced by the structural formula by conventional chemical methods. Generally, the salts are prepared by reacting the free base with stoichiometric amounts of, or with an excess of, the desired salt-forming inorganic or organic acid in a suitable solvent or various combinations of solvents. For example, the free base can be dissolved in a mixed aqueous solution of the appropriate acid and the salt recovered by standard techniques, for example, by evaporation of the solution. Alternatively, the free base can be charged into or organic solvent such as a lower alkanol, a symmetrical or asymmetrical ether containing 2 to 10 carbon atoms, an alkyl ester, or mixtures thereof, and the like and then it is treated with the appropriate acid to form the corresponding salt. The salt is recovered by standard recovery techniques, for example, by filtration of the desired salt or spontaneous separation from the solution, or it can be precipitated by the addition of a solvent in which the salt is insoluble and recovered therefrom.

Examples of suitable inorganic and organic solvents for performing the various reactions include any inorganic or organic solvent that does not adversely affect the reactants or the resulting product, including halogenated solvents such as methylene chloride, chloroform, carbon tetrachloride, ethylene chloride, ether solvents such as diethyl ether, dimethyl ether, and other solvents such as tetrahydrofuran, dioxane, diglyme, n-hexane, cyclooctane, benzene, heptane, cyclohexane; mixtures thereof, and the like aliphatic, cycloaliphatic and aromatic hydrocarbon solvents, water, acidified aqueous solutions, mixed organic and inorganic solutions, ethyl acetate, propyl acetate, and the like.

The bio-affecting HAC's from which the prodrugs of the present invention can be derived are legion. In essence, any compound which contains at least one benzene ring having at least one hydroxy group directly attached to the ring and which is biologically active can be derivatized according to the invention to afford the corresponding prodrugs of formula (A). Specifically, included are the corresponding derivatives of natural sympathetic or sympathomimetic amines. Also, as will be clear from the discussion and examples which follow, in some cases the parent HAC contain reactive moieties in addition to the hydroxyaromatic group(s) which should be protected during the reaction which forms the Z CR'R" ethers. The protecting groups are then subsequently removed to afford the desired compounds.

One important group of bio-affecting HAC which can be derivatized according to the present invention consists of the sympathomimetic amines or adrenergic agents and structurally related compounds. Especially significant members of this group are hydroxyamphetamine, hydroxyamphetamine hydrobromide, metaraminol, metaraminol bitartrate, phenylephrine hydrochloride, oxymetazoline hydrochloride, albuterenol (albuterol), carbuterol hydrochloride, deterenol hydrochloride, quinterenol sulfate, soterenol, sulfonterol hydrochloride, isoxuprine hydrochloride (isoxsuprine), nylidrin hydrochloride, bamethan, bamethan sulfate, mesuprine hydrochloride and ritodrine hydrochloride. Examples of other parent phenols in this category include, without limitation, benserazide, dimethophrine, dl-etilefrin, hordenine, p-hydroxyephedrine, ifenprodel, leptodactyline chloride, leptodactyline picrate, norfenefrine, octopamine, phentolamine, pholedrine, synephrine, tyramine, and ethamivan.

Another significant group of HAC which can be derivatized to form the compounds of formula (A) includes salicyclic acid, its derivatives and chemically related compounds, e.g., non-steroidal anti-inflammatory agents, non-narcotic analgesics, antipyretics, antituberculars, antimicrobials, antibacterials, antifungals, antirheumatics, sunscreening agents, anthelmintics, anesthetics, topical antiinfectives, and miscallaneous other structurally related compounds. For example, there can be mentioned acetaminophen, eugenol, p-animosalicylic acid, 4-benzamidosalicylic acid, calcium benzoylpas, biphenamine, buclosamide, homosalate, hydroxyprocaine, methyl salicylate, oxybenzone, dioxybenzone, phenyl aminosalicylate, salicyl alcohol (saligenin), salicylamide, salicylic acid, salicylsalicylic acid (salsalate), sodium salicylate, difunisal, dibromsalan, fursalan, metabromsalan, bensalan, salethamide, and salcolex. Other examples of parent compounds encompassed by this group include p-amino-salicylic acid hydrazide, ammonium salicylate, 5-bromo-4'-chlorosalicylanilide, 5-bromosalicylhydroxamic acid, p-butylaminosalicylic acid 2-diethylaminoethyl ester, 3'-carboxy-4-hydroxycinchophen, choline salicylate, 3,5-dibromosalicylaldehyde, fluorosalan, flopropione, gallacetophenone, gentisic acid, 4-hydroxyisophthalic acid, hydroxytetracaine, N-isopropylsalicylamide, niclosamide, osalmid, oxyclozanide, oxyphenbutazone, Pascaine ® (hydroxyprocaine p-aminosalicylate), phenetsal, phenyl salicylate, resorantel, salacetamide, salicyl, salicylanilide, salazosulfadimidine, salazosulfamide, salicylazosulfapyridine, 4-salicyloxymorphine, 4-sulfanilamidosalicylic acid, o-thymotic acid, 3',4',5-trichlorosalicylanilide, xipamide, amidan, bromosaligenin and 3,5-diiodosalicylic acid.

Yet another important group of parent HAC comprises the synthetic (non-steroidal) estrogens, for example, benzestrol, dinestrol, diethystilbestrol, hexestrol, mestilbol and promethestrol.

Another group of HAC comprises Vitamins K and E and structurally related compounds having Vitamin K or E type activity. In the Vitamin K (antihemorrhagic) sub-group, one can mention Vitamin $K_5$, 4-acetamido-2-methyl-1-napthol and juglone. In the Vitamin E group, in addition to Vitamin E ($\alpha$-tocopherol), one can mention $\beta$-tocopherol, $\gamma$-tocopherol, $\delta$-tocopherol and tocol antioxidant as suitable parent phenols for use in the present invention.

Another very significant group of HAC which can be derivatized to form the prodrugs of formula (A) include morphine and other narcotic analgesics and narcotic antagonists. Particularly significant members of this group are apomorphine, hydromorphone hydrochloride, ketobemidone, morphine, morphine hydrochloride, morphine N-oxide, nalorphine hydrochloride, naloxone hydrochloride, pentazocine, levorphanol tartrate, metopon hydrochloride, buprenorphine hydrochloride, butophanol, cyclazocine, profadol hydrochloride, levallorphan tartrate, alazocine, nalbufine hydrochloride, oxilorphan, nalmexone hydrochloride, naltrexone and apocodeine. Further illustrations of members of this group are cyclorphan, desomorphine, dihydromorphine, 3-hydroxy-N-methylmorphinane, hydroxypethidine, levophenacylmorphan, metazocine, norlevophanol, normorphine, oxymorphone, phenazocine, penomorphan, pholcodine and cyprenorphine.

Another group of bio-affecting HAC from which the instant prodrugs can be derived consists of the tetracycline-type antibiotics. Particularly noteworthy members of this group include tetracycline, tetracycline hydrochloride, chlortetracycline, demeclocycline, doxycycline, oxytetracycline, apicycline, clomocycline, guamecycline, methacycline, rolitetracycline, rolitetracycline nitrate sequihydrate, sancycline, lymecycline, mepicycline and minocycline.

A further group of bio-affecting HAC which can be derivatized according to the present invention comprises 8-hydroxyquinoline and structurally related compounds, which variously possess activities such as antibacterial, fungistatic, antimalarial and antiamebic. Many of these compounds find utility as anti-infectives. Especially important members of this class include chlorquinaldol, 5-chloro-8-quinolinol, clamoxyquin, 8-hydroxy-7-iodo-5-quinolinesulfonic acid, iodochlorhydroxyquin, octoquin methylsulfate and oxyquinoline benzoate. Exemplary of other members of this class are 8-hydroxyquinoline, chloroxine, amodioquin, diiodohydroxyquin and nitroxoline.

Another important group of bio-affecting HAC comprises the anthelmintics, which often consist of at least two variously substituted benzene rings, attached directly to each other or via a bridge (e.g., —S—, —CH$_2$—, etc.), at least one of the rings bearing at least one nuclear hydroxy group. However, some anthelmintics are one-ring systems, while yet others contain two or more fused rings. Illustrative of anthelmintics which can be derivatized according to the present invention are bithionol, dichlorophene, 4-hexylresorcinol, rafoxanide, aspidin, aspidinol, carvacrol, harmalol, menichlopholan, 2-naphthol, disophenol and thymol.

Still another significant group of bioaffecting HAC whose members can be derivatized according to the present invention comprises relatively simple one ring (e.g., the phenols) and bridged systems (e.g., the salans). Many of the members of this group have germicidal, fungicidal, etc., properties and are useful as topical antiinfectives, for example, fentichlor, phenol, pentachlorophenol, resorcinol, hexachlorophene, chlorophene, dibromsalan, bensalan, fursalan, metabromsalan, tribromsalan, dimethylcyclohexyl phenol, 6-n-amyl-m-cresol, acetomeroctol, butylparaben, 4-chloro-m-cresol, p-chlorophenol, chlorothymol, 4-chloro-3,5-xylenol, chloraphine, p-cresol, 3,5-dibromo-4-hydroxybenzenesulfonic acid, Dowicide 9, o-hydroxyphenylmercuric chloride, methylparaben, fluorosalan, p-pentyloxyphenol, 2-phenyl-6-chlorophenol, o-phenylphenol, picric acid, propylparaben, pyrocatechol, pyrogallol, 3,4,5,6-tetrabromo-o-cresol, 2,4,6-tribromo-m-cresol, 2,4,5-trichlorophenol and 2,4,6-trichlorophenol. Other members of this structural group include anacardiol (analeptic), apocynin (cardiotonic), gallic acid (astringent), guaiacol (expectorant), bufeniode (antihypertensive), capsaicin (counterirritant), cotoin (antidiarrheal), cyclovalone (chlorectic), dobesilate calcium (vasotropic), fendiazole (hypnotic), $\alpha$-(p-methoxyphenol)-$\alpha$-2-pyridyl-p-cresol (cathartic), mexenone (sunscreen), monobenzone (depigmentor), orthocaine (topical anesthetic), paroxypropione (pituitary gonadotropic hormone inhibitor), 3-pentadecylcatechol (allergen), phenolphthalol (cathartic), phloroglucinol (antispasmodic), probucol (antichloesteremic), TFM (sea lamprey killer), 3,4-6-trichloro-2-nitrophenol (sea lamprey killer), urushiol (allergen, poison ivy desensitizer), vanitiolide (chloeretic), hydroquinone (depigmenting agent) and monobenzone (depigmenting agent).

Yet another significant group of HAC which can be derivatized to form compounds of formula A consists of antibiotic/antibacterial/antimicrobial agents, for example, the rifamycins (e.g., rifamycin B, rifamycin SV), xanthocillin (X, $Y_1$ and $Y_2$) and amoxicillin. Other members of this group include celesticetin, chartreusin, novobiocin, resistomycin, rifamide, rifampin, albofungin, Formecin A, hygromycin, Acroteben ® (anti-tubercular), amindan, antranorin, azosulfamide, diathymosulfone, Flavoteben (anti-tubercular), 1-isonicotinoyl-2-salicylidenehydrazide (anti-tubercular), lasalocid, myxin (antifungal), siccanin (antifungal), tyrocidine A, tyrocidine B, tyrocidine C and antinorhordine.

Another important group of HAC comprises antineoplastic agents, for example, mycophenolic acid, anthramycin, carvicarcin, 5-hydroxytryptophan and pactamycin.

Yet another noteworthy group of HAC which can be derivatized according to the present invention are typified by an anthraquinone or anthracene-type structure. Exemplary of this group are emodin, aloeemodin, aloin, danthron and frangulin, all of which have utility as cathartics. Other members of this structural group include doxorubicin (antibiotic/neoplastic), anthrarobin (parasiticide) and dithranol (antifungal).

Another group of parent bio-affecting HAC comprises compounds containing a benzopyran-type structure, for example, catechin (astringent), baicalein (astringent), 3-dibutylaminomethyl-4,5,6-trihydroxy-1-isobenzofuranone (antihistaminic), eridictyol (expectorant), eupatorin (emetic), formononetin (diuretic) and hymecromone (choleretic, antispasmodic).

Yet other bio-affecting HAC which can be derivatized to form the prodrugs of the invention include benzofuran-type, isobenzofuran-type, indanetype, and other fused systems, which optionally contain one or more hetero atoms. Such phenols include benzarone (for increased capillary fragility), benzbromarome (uricosuric), benziodarone (coronary vasodilator), bufotenin (hallucinogen), bismuth sugallate (astringent, antacid), coumetarol (anticoagulant), 2-(2-hydroxy-1-naphthyl)cyclohexanone (anti-tussive), quercetin (to decrease capillary fragility), rutin (to decrease capillary fragility), tioxolone (antiseborrheic), troxerutin (for venous disordics) and chlorindanol (spermicide). Other such phenols include phenolphthalein, phenolsulfonphthalein, phenoltetrachlorophthalein and sulfobromophthalein sodium, all of which are useful as cathartics and/or diagnostics for renal function. Still other such phenols include salsoline (antihypertensive), meralein sodium (topical anti-infective), scarlet red (promotes wound healing), synhexyl (psychotomimetic), umbelliferone (sunscreen), serotonin (smooth muscle stimulant) and $\Delta^1$ tetrahydrocannabinol (hallucinogen). Other bio-affecting phenols of relatively complex structures include boldine (diuretic), bulbocapnine (for Meniere's disease and other muscular tremors), ellagic acid (hemostatic), hypericin (antidepressant), neohesperidin dihydrochalcone (sweetening agent), polyamine-methylene resin (antacid), silybin (in liver dysfunction), d-tubocurarine chloride (skeletal muscle relaxant, diagnostic aid for myasthenia gravis), zearalenone and zeranol (anabolics), and fluorescein and fluorescein (diagnostics for corneal trauma).

Yet another group of HAC which can be derivatized according to the present invention include tyrosine and thyroxine and their derivatives. These include 3,5-dibromotyrosine, 3,5-diiodotyrosine and 3-fluoro-4-hydroxyphenylacetic acid (thyroid inhibitors); tyrosine, m-tyrosine and dipeptides and polypeptides containing same; α-methyl-m-tyrosine (inhibitor of catecholamine synthesis); α-methyl-ptyrosine (tyrosine hydroxylase inhibitor, L-form as antihypertensive); L-α-aspartyl-L-tyrosine methyl ester (sweetening agent); hinderin (thyroid inhibitor); sodium levothyroxine (thyroid hormone); thyroxine (L-form as thyroid hormone, D-form as anticholesteremic); dextrothyroxine sodium (anticholesteremic); 3,3',5-triiodothyroacetic acid and 3,5,3'-triiodothyronine (thyroid replacement therapy); and 3,3',5-triiodothyropropionic acid (in hypercholesterolemia, myxedema or gout).

Other bio-affecting HAC which can be derivatized according to the present invention include various antimalarials, antiamebics, antiprotozoals, poultry coccidiostats and related veterinary products, e.g., bebeerine (antimalarial), bialamicol (antiamebic), cephaeline (antiamebic), diloxanide (antiamebic), lasalocid (poultry coccidiostat) and phlorizin (antimalarial). Also to be mentioned here are acetarsone (antitrichomonal; antihistomonad in turkeys; spirochetocide in turkeys), acetarsone diethylamine salt (antisyphilitic; for swine dystentery), arsphenamine (antisyphilitic), arsthinol (antiprotozoal), dichlorophenarsine hydrochloride (antisyphilitic), neoarsphenamine (for equine petechial fever), oxophenarsine hydrochloride (antitrypanosamol), phenarsone sulfoxylate (antiamebic), roxarsone (control of enteric infections; to improve growth and feed efficiency), spirotrypan (antisyphilitic, antitrypanosomal), and sulfarsphenamine (antisyphilitic).

Another group of HAC for possible derivation according to the present invention include 2-cyclohexyl-2,6-dinitrophenol (insecticide), 2,4-dinitrophenol (weed killer), 4,6-dinitro-o-cresol (selective herbicide, insecticide), MON-0585 (insecticide, especially for mosquito larvae) and pentachlorophenol (insecticide for termite control).

In addition, the present invention contemplates prodrugs corresponding to formula (A) but wherein drug -O-mono- or polydeprotonated residue of a bio-affecting heteroaromatic compound bearing at least one nuclear hydroxy substituent. The parent heteroaromatic which can be derivatized according to the present invention can be mono- or polycyclic. In the latter case, one or more rings will be heteroaromatic. Exemplary of such compounds are clopidol, buquinolate and proquinolate (all of which are poultry coccidiostats), pyridoxine hydrochloride (Vitamin B₆ hydrochloride), and structurally related compounds such as pyrisuccideanol (an antidepressant) and pyrithioxin (a neurotropic agent). Accordingly, preferred parent heteroaromatics which can be derivatized according to the invention contain at least one pyridine or quinoline ring system bearing at least one nuclear hydroxy substituent on the heteromatic ring.

In the discussion which follows, for the sake of convenience, the synthetic methods, pharmaceutical compositions, etc., will be discussed in terms of the HAC of the invention. It is to be understood, however, that this discussion is equally applicable to the corresponding compounds in which drug —O— is the mono- or polydeprotonated residue of a bio-affecting heteroaromatic compound bearing at least one nuclear hydroxy substituent.

In the above structural formula, $Z$ is preferably the dehydro residue of the compound $ZH$, wherein the pKa of $ZH \rightarrow Z^- + H_+$ is the range of from 1.0 to 12.0. Illustrative of such leaving groups are those described by J. March, "Advanced Organic Chemistry, 3rd Ed., pp. 310–316 (1985); J. Chem. Res., Vol. 12, p. 198 (1979); Tetrahedron, Vol 36, p. 679 (1980) and Angew. Chem. Int. Ed. Engl. Vol, 23, p. 420 (1984); e.g.,

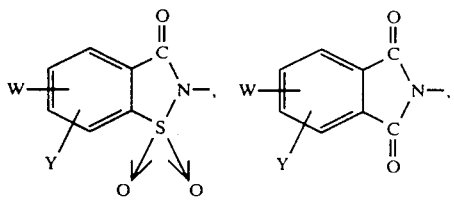

-continued

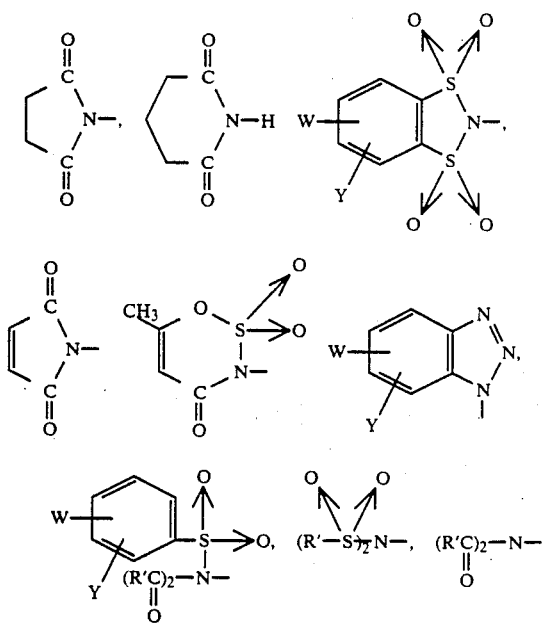

wherein W and Y may be the same or different and are selected from the group consisting of COR''', COOR''', CON(R''')₂, N(R''')₂, OR''', halogen, SR''', NO₂ and R''' wherein R''' has the meanings ascribed above.

The compounds X—CR'R" Z may be prepared by the reaction of ZH with O=C—R'R" to yield HOCR'R" Z which is then allowed to react with a chlorinating agent (e.g., SOCl₂, PCl₅, POCl₃, etc.) to yield ClCR'R" Z where X=Cl. The latter can be converted to X=I by the reaction of ClCR'R" Z with NaI in acetone. HOCR'R" Z can be converted to X=Br by reaction with SOBr₂, etc., or to X=tosyl by reaction with tosyl chloride in the presence of an acid scavenger such as pyridine.

The above-described prodrugs may be prepared by reacting n equivalents of the above compound having the structural formula:

wherein X is an anion such as Cl, Br, I, tosyl, etc., and R', R" and Z have the above ascribed meanings with the HAC drug DRUG-(OH)ₙ in the presence of an acid scavenger (e.g., Et₃N, K₂CO₃) according to the following reaction formula:

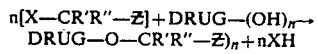

The reaction is preferably conducted in an inert solvent for the reactants and reaction products (e.g., acetone, methylethylketone, 3-hexanone, etc.) at 0° C. to the reflux temperature of the solvent for 1-48 hours.

It will be apparent to those skilled in the art that the HAC may contain functional groups besides the hydroxyaromatic groups which may be subject to alkylation under the above conditions. It will, accordingly, be necessary to transiently protect such groups with conventional protecting groups during formation of the prodrugs of the invention. Protecting groups for the various functional groups are well known in the art and are litsted, for example, in Theodora W. Greene's book on "Protective Groups in Organic Synthesis", John Wiley & Sons, N.Y. (1981).

EXAMPLE 1

This example illustrates the preparation of the prodrugs of the invention using p-nitrophenol as a model phenolic drug and saccharinylmethyl ether as the OH-protecting agent in the following reaction scheme:

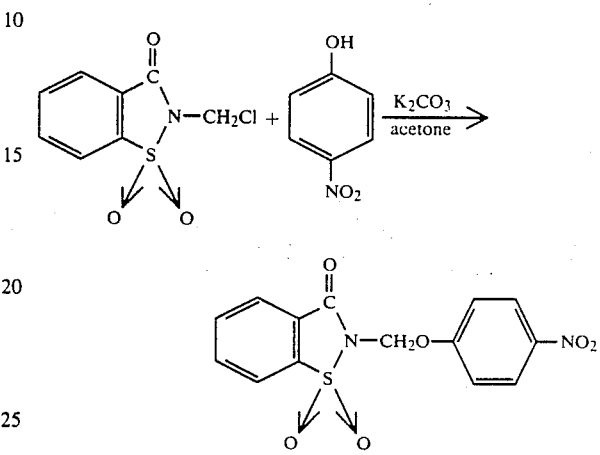

The product hydrolyzed in pH=7.1 buffer at room temperature with a half-life of about 17 min. (pKa of ZH=1.6).

The compounds:

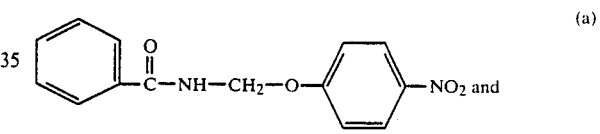

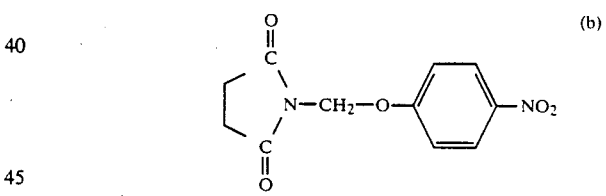

were prepared similarly to the above product and their hydrolytic properties under similar conditions were evaluated. Compound (a) was completely stable at pH=7.1 (pKa of ZH=16) whereas compound (b) hydrolyzed with a half-life of about 6 hours (pKa of ZH=9.6).

The compounds of the following examples were prepared according to the following general method:

To an acetone (20 ml) solution of chloromethylsaccharin (2.3 g, 0.010 mole) and an equivalent amount of anhydrous sodium iodide (1.5 g, 0.010 mole) was added anhydrous potassium carbonate (1.4 g, 0.010 mole) and the desired phenol (0.010 mole) or catechol (0.0050 mole). The suspension that resulted was stirred at room temperature for one to two days. The suspension was diluted to 150 ml with dichloromethane and filtered. The filtrate was concentrated and the concentrate either was crystallized directly from acetone or was partitioned between dichloromethane and aqueous sodium hydroxide. In the latter case the dichloromethane solution was separated, dried over sodium sulfate and concentrated; then the concentrate was crystallized from acetone.

EXAMPLE 2

4-Methoxy-1-[1',1'3'-trioxo-(2'H)-1',2'-benziso-thiazol-2-yl]methoxybenzene mp 117°–119°, 31% yield of product, mp 121°–122° recrystallized from acetone, 24% yield of analytically pure product; TLC (silica gel, ether) $R_f=0.48$; NMR (CDCl$_3$) δ 8.2–7.8 (m, 4, aromatic-H), 7.0 (ABq, 4, J = 6 HZ, $\Delta V_{AB}=15$ Hz, aromatic-H), 5.78 (s, 2, N—CH$_2$—O) and 3.77 (s, 3, CH$_3$O).

Anal. Calcd for $C_{15}H_{13}NO_5S$: C, 56.41; H, 4.10, N, 4.39. Found: C, 56.33; H, 4.14; N, 4.38.

EXAMPLE 3

[1',1',3'-Trioxo-(2'H)-1',2'-benzisothiazol-2'-yl]-methoxybenzene mp 118°–120°, 41% of product, mp 123°–124° recrystallized form acetone, 20% yield of analytically pure product; TLC (silica gel, ether) $R_f=0.48$; NMR (CDCl$_3$) δ 8.25–7.8 (m 4, aromatic-H), 7.55–7.0 (m, 5, aromatic-H), and 5.75 (s, 2, N—CH$_2$—O).

Anal. Calcd for $C_{14}H_{11}NO_4S$: C, 58.12, H, 3.83, N, 4.84. Found: C, 57.97; H, 3.87; N, 4.82.

EXAMPLE 4

4-Nitro-1-[1',1',3'-trioxo-(2'H)-1',2'-benzisothiazol-2'-yl]methoxybenzene mp 162°–164°, yield of analytically pure product; TLC (silica gel, ether) $R_f=0.41$; NMR (CDCl$_3$) δ 8.2–7.8 (m, 4 aromatic-H), 7.72 (ABq, 4, J=6 Hz, $\Delta V_{AB}=54$ Hz, aromatic-H), 5.92 (s, 2, N—CH$_2$—O).

Anal. Calcd for $C_{14}H_{10}N_2O_6S$: C, 50.29; H, 3.02; N, 8.38. Found: C, 50.21; H, 3.03; N, 8.33.

EXAMPLE 5

Acetylamino-1-[1',1',3'-trioxo-(2'H)-1',2'-benziso-thiazol-2'-yl]methoxybenzene mp 167°–170°; 47% yield of product; mp 170°–171°, 38% yield of analytically pure product; TLC (silica gel, ether: CH$_2$Cl$_2$, 8:2) $R_f=0.64$; NMR (CDCl$_3$) δ 9.3–9.0 (m, 1, N-H), 8.2–7.7 (m, 4, aromatic-H), 7.3 (ABq, 4, J=6 Hz, $\Delta V_{AB}=29$ Hz, aromatic-H), 5.75 (s, 2, N—CH$_2$—O), and 2.1 (s, 3, CH$_3$CONH).

Anal. Calcd. for $C_{16}H_{14}N_2O_5S$: C, 55.48; H, 4.07; N, 8.09. Found: C, 55.56; H, 4.11; N, 8.03.

EXAMPLE 6

1,2-Bis[1',1',3'-trioxo-(2'H)-1',2'-benzisothiazol-2'yl]methoxybenzene mp 151°–153°, 31% yield of product; mp 153°–154°, 22% yield of analytically pure product; TLC (silica gel, ether) $R_f=0.30$; NMR (CDCl$_3$) δ 8.2–7.85 (m, 8, aromatic-H), 7.35–6.9 (m, 4, aromatic H), and 5.88 (s, 4, N—CH$_2$O).

Anal. Calcd for $C_{22}H_{16}N_2O_8S_2$: C, 52.79; H, 3.22; N, 5.60. Found: C, 52.54; H, 3.24; N, 5.54.

EXAMPLE 7

3-[1',1',3'-trioxo-(2'H)-1',2'-benzisothiazol-2-yl]-methyl foam, 53% yield after column chromatography on SilicAR-CC-7 using ether as the eluent; TLC (silica gel, ether) $R_f=0.31$; NMR (CDCl$_3$) δ 8.2–7.8 (m, 4, aromatic-H), 6.87 (s, 1, aromatic-H), 7.1 (ABq, 2, J=6 Hz, $\Delta V_{AB}=17$ Hz, aromatic-H), 5.8 (s, 2, N—CH$_2$—O), 3.8–3.6 (m, 1, CH—OH), and 0.76 (s, 3, CH$_3$—C).

Anal Calcd for $C_{26}H_{29}NO_5S$: C, 66.78; H, 6.25; N, 3.00. Found: C, 66.50; H, 6.33; N, 2.94.

EXAMPLE 8

3-[1',3'-trioxo-(2'H)-1',2'-benzisothiazol-2-yl]methyl-pentazocine

Oil, 60% yield after column chromatography on Florasil using dichloromethane as the eluent; TLC (silica gel, acetone) $R_f=0.5$; NMR (CDCl$_3$) δ 8.1–7.8 (m, 4, aromatic-H), 7.05–6.87 (m, 3, aromatic - H), 5.75 (s, 2, N—CH$_2$—O), 5.48–5.12 (m, 1, CH=C), 1.68 (d, J-4HZ, 6, (CH$_3$)$_2$C=C), 1.33 (s, CH$_3$—C—) and 0.82 (d, J=5HZ, 3, CH$_3$—C—H).

The same general procedure as was used for the saccharinylmethyl ethers was used for the preparation of the following succinimidylmethyl ethers.

EXAMPLE 9

4Nitro-1-succinimidylmethoxybenzene mp 156°–158°, 66% yield, TLC (silica gel, ether) $R_f=0.18$; NMR (CDCl$_3$) δ7.72 (ABq, 4, J=6 Hz, $\Delta V_{AB}=63$ Hz, aromatic-H), 5.58 (s, 2, N—CH$_2$O), and 2.83 (s, 4, O=CCH$_2$CH$_2$=O).

Anal. Calcd for $C_{11}H_{10}N_2O_5$: C, 52.80; H, 4.03; N, 11.20. Found: C, 52.76, H, 4.04; N, 11.16.

EXAMPLE 10

Succinimidylmethoxybenzene mp 88°–91°, 27% yield; TLC (silica gel, ether) $R_f=0.29$, NMR (CDC$_3$) δ7.5–6.95 (m, 5, aromatic-H), 5.48 (s, 2, N—CH$_2$—O), and 2.76 (s, 4, O=CCH$_2$CH$_2$C=O).

Anal. Calcd for $C_{11}H_{11}NO_3$:C, 64.39; H, 5.40; N, 6.83. Found: C, 64.19; H, 5.46; N, 6.77.

EXAMPLE 11

4-Methoxy-1-Succinimidylmethoxybenzene mp 86°–88°, 30% yield; TLC (silica gel, ether) $R_f=0.21$; NMR (CDCl$_3$) δ6.95 (ABq, 4, J=6 Hz, $\Delta V_{AB}=10$ Hz, aromatic-H), 5.43 (s, 2, N—CH$_2$O), 3.78 (s, 3, OCH$_3$), and 2.77 (s, 4, O=CCH$_2$CH$_2$C=O).

Anal. Calcd for $C_{12}H_{13}NO_4$: C, 61.28; H. 5.60; N, 6.00. Found: C, 61.19: H, 5.62; N, 5.89.

The same general procedure as was used for the saccharinylmethyl ethers was used for the preparation of the following phthalimidylmethyl ethers.

EXAMPLE 12

4-Methoxy-1-phthalimidylmethoxybenzene mp 149°–150°, 47% yield; TLC (silica gel, ether) $R_f=0.48$; NMR (CDCl$_3$) δ8.03–7.7 (m, 4, aromatic-H), 6.94 (ABq, 4, J=6 Hz, $\Delta V_{AB}=11.5$ Hz, aromatic-H), 5.60 (s, 2, N—CH$_2$O), and 3.75 (s, 3, OCH$_3$).

Anal. Calcd for $C_{16}H_{13}NO_4$: C, 67.80; H, 4.63; N, 4.94. Found: C, 67.89; H, 4.66; N, 4.93.

EXAMPLE 13

4-Nitro-1-phthalimidylmethoxybenzene mp 160°–161°, 48% yield, TLC (silica gel, ether) $R_f=0.45$; NMR (CDCl$_3$) δ8.1–7.7 (m, 4, aromatic-H), 7.75 (ABq, 4, J=6 Hz, $\Delta V_{AB}=60$ Hz, aromatic-H), 5.80 (s, 2, N—CH$_2$—O).

Anal. Calcd for $C_{15}H_{10}NO_5$: C, 60.20; H, 3.34; N, 9.36. Found: C, 60.33; H, 3.43; N, 9.32.

EXAMPLE 14

Phthalimidylmethoxybenzene mp 140°–143°, lit (J. Org. Chem., (1963) 28, 2925) mp 140°–141°, 52% yield; TLC (silica gel, ether) $R_f = 0.50$; NMR (CDCl$_3$) $\delta 8.0$–7.7 (m, 4, aromatic-H), 7.5–6.95 (m, 5, aromatic-H), and 5.72 (s, 2, N—CH$_2$O).

Anal Calcd. for $C_{15}H_{11}NO_3$; C, 71.15; H, 4.38; N, 5.53. Found: C, 71.23; H, 4.41; N, 5.49.

I claim:

1. A pharmaceutically acceptable prodrug of a biologically active, therapeutically effective hydroxyaromatic compound (HAC) drug, said prodrug being selected from the group consisting of (A) compounds having the structural formula:

DRUG$\pmb{-}$[O—CR'R"—Z]$_n$ wherein:
DRUG—O— is the HAC O-dehydro residue of the drug;

R' and R" may be the same or different and are selected from the group consisting of H, cycloalkyl groups having up to 10 carbon atoms, straight or branched chain alkyl, alkenyl or alkynyl groups of 1 to 10 carbon atoms, wherein the chains thereof (1) may be interrupted by at least one N, S or O atom, or (2) may be substituted by at least one group selected from the group consisting of COR''', COOR''' and CON(R''')$_2$, hydrocarbyl aryl groups, aryl groups substituted by at least one group seelcted from teh goup consisting of COR''', COOR''', CON(R''')$_2$, N(R''')$_2$, OR''', halogen, SR''', NO$_2$ and R''', mono- and bi-cyclic saturated or unsaturated heterocyclic rings, each ring consisting of 3 to 7 members selected from the group consisting of carbon, nitrogen, oxygen and sulfur, CN, COR''', COOR''', CON(R''')$_2$ and C(halogen)$_3$;

R''' is selected from the group consisting of cycloalkyl groups having up to 10 carbon atoms, straight or branched chain alkyl, alkenyl and alkynyl groups having 1 to 10 carbon atoms, straight or branched chain alkyl, alkenyl and alkynyl groups of 1 to 10 carbon atoms wherein the chains thereof may be interrupted by at least one N, S or O atom, hydrocarbyl aryl groups, and in the case of —N(R''')$_2$ taken with the other R''' group an N is a mono- or bi-cyclic saturated or unsaturated hetereocyclic ring, wherein each ring consists of 3 to 7 members selected from the group consisting of carbon, nitrogen, oxygen and sulfur;

Z is a displaceable leaving group and is the dehydro residue of the compound Z—H wherein the pKa of Z—H → Z$^-$ + H$^+$ is the range of from 1.0 to 12.0; and n is an integer in the range of from 1 to 3, and (B) pharmaceutically acceptable salts thereof;

said prodrug having enhanced stability against premature metabolism upon oral administration and being chemically hydrolyzable to the HAC drug.

2. A pharmaceutical composition in unit dosage form adapted for oral or topical administration to a human or non-human animal in need thereof comprising a therapeutically effective amount of a prodrug of claim 1 and a pharmaceutically acceptable carrier therefor.

3. A method of treatment comprising orally or topically administering to a human or non-human animal in need thereof a therapeutically effective amount of a prodrug of claim 1.

* * * * *

UNITED STATES PATENT AND TRADEMARK OFFICE
CERTIFICATE OF CORRECTION

PATENT NO. : 5,001,115
DATED : March 19, 1991
INVENTOR(S) : Kenneth B. Sloan

It is certified that error appears in the above-identified patent and that said Letters Patent is hereby corrected as shown below:

Column 15, line 34 of claim 1: delete "seelcted" and insert --selected--; delete "teh goup" and substitute --the group--.

Column 16, line 13 of claim 1: delete "an" and insert --and--.

Column 16, line 21, before "is" insert a space and after "is" insert --in--.

Signed and Sealed this

First Day of September, 1992

Attest:

DOUGLAS B. COMER

*Attesting Officer*     *Acting Commissioner of Patents and Trademarks*